United States Patent [19]
Baker et al.

[11] Patent Number: 5,359,907
[45] Date of Patent: Nov. 1, 1994

[54] METHOD AND APPARATUS FOR DRY PARTICLE ANALYSIS

[75] Inventors: Jeffrey P. Baker, Poway; Steven C. Mott; Craig A. Wright, both of San Diego, all of Calif.

[73] Assignee: Horiba Instruments, Inc., Irvine, Calif.

[21] Appl. No.: 975,019

[22] Filed: Nov. 12, 1992

[51] Int. Cl.$^5$ .................... G01N 15/02; G01N 21/85
[52] U.S. Cl. .................... 73/865.5; 356/335; 356/438
[58] Field of Search ............... 356/335, 336, 438, 440; 73/865.5, 23.33, 23.41, 23.42, 24.03, 24.06, 864.81

[56] References Cited

U.S. PATENT DOCUMENTS

| | | | |
|---|---|---|---|
| H257 | 4/1987 | Barditch et al. | 239/124 |
| 3,478,597 | 11/1969 | Merigold et al. | 73/865.5 |
| 3,744,297 | 7/1973 | Hanson et al. | 73/24.03 |
| 3,833,305 | 9/1974 | Porter et al. | 356/438 |
| 3,938,259 | 2/1976 | Ormos et al. | 34/10 |
| 3,939,714 | 2/1976 | Miller, Jr. | 73/424 |
| 4,047,814 | 8/1977 | Westcott | 356/38 |
| 4,070,765 | 1/1978 | Hovmand et al. | 34/10 |
| 4,154,111 | 5/1979 | Anderson et al. | 73/865.5 |
| 4,178,796 | 12/1979 | Zwicker et al. | 73/865.5 |
| 4,213,325 | 7/1980 | Tumanov et al. | 73/1 G |
| 4,413,911 | 11/1983 | Rice et al. | 356/438 |
| 4,432,649 | 2/1984 | Krause | 356/438 |
| 4,515,274 | 5/1985 | Hollinger et al. | 209/3.1 |
| 4,564,803 | 1/1986 | Loren et al. | 324/71.1 |
| 4,983,038 | 1/1991 | Ohki et al. | 356/246 |
| 5,090,233 | 2/1992 | Kogure et al. | 73/865.5 |
| 5,163,202 | 11/1992 | Kawakami et al. | 356/438 |
| 5,200,629 | 4/1993 | Kaiblinger | 356/438 |
| 5,231,865 | 8/1993 | McDermott et al. | 73/865.5 |

FOREIGN PATENT DOCUMENTS 8901143  2/1989  WIPO ................ 73/865.5

Primary Examiner—Hezron E. Williams
Assistant Examiner—George M. Dombroske
Attorney, Agent, or Firm—Poms, Smith, Lande & Rose

[57] ABSTRACT

A dry particle analyzer includes a vibrating sieve cup drizzling particles downwardly with first and second sheath air flows provided to separate the particles from boundary walls and to form the drizzling particles into a curtain for optical analysis. The particles drop vertically as a drizzle with gravitational assistance from a bulk sample to the analysis passage, after which their direction of movement is changed to horizontal and then upward for removal from the analyzer.

21 Claims, 3 Drawing Sheets

METHOD AND APPARATUS FOR DRY PARTICLE ANALYSIS

FIELD OF THE INVENTION

The present invention relates to dry particle analysis. More particularly, the present invention relates to methods and apparatus for analysis by optical means of a physical characteristic, such as particle size distribution, of a bulk sample of particulate material. Analysis of the physical characteristic is accomplished by entrainment of the particulates as a drizzle in ambient air without the use of a conventional liquid particle dispersant, or liquid stirring devices.

BACKGROUND OF THE INVENTION

The art of particle analysis includes two broad categories of apparatus. On the one hand, analysis of particulates native in liquid has lead to the development of "wet process" particle analyzers which use various techniques to determine certain characteristics of the particulates in liquid suspension. Illustrative of this type of analyzer is that described in U.S. Pat. No. 4,047,814, to V. Westcott wherein particulates suspended in a liquid are caused to "plate out" on a substrate by application of a force field. The force field may be magnetic or electrostatic, for example. Analysis of the particulates is accomplished after fixing them on the substrate and drying preparatory to optical inspection. An illustrative example of the use of the Westcott invention is directed to analysis of metallic wear particles in lubricating oil from an engine.

An alternative technology, that of electromagnetic radiation (i.e., light) obscuration, scattering and diffraction analysis, allows particulates to be analyzed in their native liquid without the need of fixing and drying as required by Westcott. With this technology, a liquid sample with particulates therein is illuminated in an analysis cell with selected light or other radiation, Analysis of the resulting forward or back light scattering, diffraction, or obscuration provides the desired indication of the size distribution of the particulates in the sample.

Of course, some particulates tend to settle out of the liquid, so that stirring devices for the liquids and particulates therein have had to be developed. Typical of this category of particle analysis devices is one by Leeds and Northrop, a unit of General Signal, Inc. For example, a particle analyzer from this company known under the name Microtrac II, as depicted and described in a 1987 brochure, includes as a stirring device a so-call, "particle circulator", which recirculates liquid with particulates therein through an analysis cell. Almost in defense of this stirring device, the particle circulator itself is stated to be free of dead spaces in which particulates could collect or settle out. Also, a common problem with this type of wet process analysis with stirring is stated to be air entrainment where bubbles are created in the carrier liquid and can interfere with the measurement. The particle circulator of the Microtrac II also assertedly solves to some extent the problem of air entrainment in the carrier liquid. Thus, it is seen that the wet process analysis of particulates has its own set of problems, and that a solution to one problem may itself impose its own deficiencies on the art.

The foregoing type of wet process particle analyzer is also applied to measurement of particulates not native to liquid by dispersing the particulates in a dispersant liquid. Of course, this expedient raises the questions of compatibility of the particulates with the dispersant liquid, for example, of wetting the particulates with the liquid, of solution of particulates or constituents thereof in the dispersant, and of agglomeration of the particulates in the liquid, to name just a few concerns. However, the degree to which the problems of wet particulate analyzers are brought to the measurement of originally dry particulates, and the degree to which these problems are solved, or remain unsolved, is the subject of ongoing debate in the art.

In view of the above, dry analysis of dry particulates, and the subsequent complete avoidance of the problems associated with the wet process particle analyzers, seems a desirable goal. Thus, many have labored to develop the other major category of particle analysis device, the dry process analyzer. For example, U.S. Pat. No. 3,269,189, of W. G. Monk, is believed to teach a device for classifying particulates by size and weight in a vacuum chamber by use of vibration and a controlled air or gas flow. At about the same time, the application of optical techniques to dry particle analysis was taught by U.S. Pat. No. 3,328,587, of T. J. A. Brown, et. al. The device of Brown maintains the particulate sample in a state of consolidation, and appears to rely for its operation only on back scatter of incident light from the sample. U.S. Pat. No. 4,563,581, of Perten discloses a later effort directed to an analyzer in which the particulate sample is also compacted in an analysis cell and back scatter alone apparently provides the available information about the sample.

U.S. Pat. No. 4,895,034, to Poole, is directed to an entirely different method of particle size analysis, that of aerodynamic and optical "time of flight" analysis. According to this teaching, particles are impelled in a cloud through a nozzle, and their size is optically measured by transit time across a known distance. Poole teaches to disburse particles as a cloud in a carrier stream of air using an air blast and agitation.

An effort directed to the analysis of particulates disbursed in a flow of air, which allows back scatter, as well as forward scatter or diffraction and obscuration techniques to be employed, is represented by the European patent application, publication number 0 144 018, having a publication date of 12 Jun. 1985. This latter effort provides an observation chamber which prepares a particulate sample in an air stream for optical analysis. The observation chamber itself relies, however, on an inflow of particulates, such as coal dust, already conveyed in an air stream. An ejector is employed to entrain additional ambient air, in addition to mixing compressed air with the particulate sample and its original conveying gas flow. How the particles are introduced from a bulk sample into the conveying gas stream is not detailed in this publication.

Another dry particle analysis device is know in the art, as depicted in a 1990 publication from Coulter Scientific Instruments, which is an operating company of Coulter Electronics, Inc. Overall, the described dry particle analyzer is an adaptation of a conventional particle analyzer previously used for liquid-borne samples. This publication briefly describes a bench-top dry particle module in which free-flowing particulates are fed from a vibratory sifter cup into the entrance of the module. The sifted particulate sample is believed to be conveyed with vacuum-induced ambient air flow in a flexible corrugated conveying tube, which tube lays generally horizontally on the bench top. The conveying tube connects to an analysis cell adapted to the conventional particle analyzer. On the laboratory bench top, the module and conveying tube are relatively large, and take up bench top space, which is always in short supply. Further, the conveying tube presents an opportunity for powder to settle out of the conveying air flow, and to coat the inside of the tube. Consequently, several questions are presented with respect to the integrity of the particulate sample when it arrives at the analysis cell. The air flow in the conveying tube would seem to be necessarily turbulent. In view of this turbulence, how can eddy currents be avoided in the tube, especially at bends in the tube? Eddy currents in the air and particle flow through the tube would likely cause relatively quiescent zones where particles could settle. Has part of the sample settled out in the conveying tube? If part of the sample does settle out in the tube, is it homogeneous to the remainder of the sample so that particle size distribution as measured is not affected? If the particulates do settle out of the conveying air flow, or plate the inside of tube because of adhesion, electrostatic attraction, or other causes, will this loss of sample be preferential to particular particle sizes?

Also, the possible settling of particulates in the conveying tube presents a cleaning problem. When the conveying tube is next used, one might reasonably question whether it was completely cleaned after the last use, or could remnants of the last test be contaminating the present test? The conveying tube is thought to be a durable component, rather than being disposable. Therefore, because the interior of the conveying tube is not accessible for cleaning other than by running a rag or bore brush through the tube, cleanliness of this tube would always seem to be in question. Also, the interior of the tube is not readily available for visual inspection of cleanliness. A glance down the tube would seem insufficient, and the use of a bore scope for visual inspection would seem way too time consuming. Thus, the dry powder module of Coulter would seem to have many disadvantages.

Still further, the vibratory feed system used by Coulter might interfere with the delicate optical system of the analyzer if these vibrations were allowed to reach the analysis cell. Audible noise from this vibratory particle feeder may also be an irritant to users of the device.

SUMMARY OF THE INVENTION

In view of the above, the present invention provides means for drizzling particles from a bulk sample thereof, means for providing a downward flow of first sheath ambient air around said drizzling particles, means for downwardly columnating the first sheath air flow and drizzling particles, means for providing a downward and columnar flow of second sheath ambient air around said columnated first sheath air and drizzled particles and substantially in velocity union therewith, and means defining a vertically downwardly extending optical analysis cell passage receiving the unified downward flow of drizzled particles and first and second sheath air for downward flow therein, whereby the drizzled particles flow downwardly continuously from said bulk sample and through said analysis cell passage means.

Further to the above, the present invention provides a dry particle analyzer apparatus and method in which a vibratory sifter or sieve cup, or other dispenser for the particulates, drizzles particulates downwardly at a selected metered rate from a bulk sample of the particulates to be analyzed into a first vertically downward flow of ambient sheath air. The stream of particulates and first sheath air is directed still downwardly along a convergent conduit effecting an increase of flow velocity through an externally surrounding plenum of second sheath air. Ambient air enters the second sheath air plenum via an air filter, and flows downwardly therefrom through a multi-cellular flow columnator around the convergent conduit. This convergent conduit includes an elongate cylindrical flow-columnating exit portion extending through the flow columnator, and each has the same total air flow resistance. Consequently, a vacuum source drawing ambient air from the convergent conduit and the second sheath air plenum produces substantially the same air flow velocity for both the first and second sheath air flows. As a result, a laminar homogeneous descending column of air is provided which includes a centralized flow stream of air including the drizzle of particles at a known location in the air flow column. Disposed below the convergent conduit and second sheath air plenum, and in sealed relation with the latter, is a planar analysis cell defining an air flow path generally of J-shape. The analysis cell defines a vertically downwardly extending analysis passage having opposite transparent windows for passage of test radiation beams perpendicular to the plane of the "J". Below the analysis passage, the analysis cell includes side walls defining a sub-critical convergent-divergent venturi nozzle shape, which turns the air and particulate flow 180 degrees at the bottom of the "J", and leads upwardly as a divergent pressure-recovery diffuser to an exit port. A vacuum source is connected to the exit port to effect the air and particulate flows through the device.

Importantly, the present dry particle analyzer method and apparatus conveys the particulates continuously vertically downwardly from their separation out of the bulk particulate sample and through the analysis passage of the cell. The particles flow through and outwardly of the cell with smooth continuous flow. Because of the first and second sheath air flows, the particulates preferably do not contact the walls of the analysis cell above the analysis passage. Further, should any particulates contact the cell walls and adhere thereto, the cell is small and easily cleaned, so that integrity of subsequent tests is not thrown into question. The flow path length from the bulk sample to the analysis passage is short, on the order of only a few inches, and is all vertical with downward flow so that virtually no opportunity exists for particulates to settle out of the conveying air flow. No dead volume exists in the air and particle flow path, which is virtually straight with no twists or bends to cause air flow turbulence and pressure losses prior to the analysis cell. Further, the cell design does not fight gravity, so that gravitational force is an assistance rather than a hindrance to delivery of the particulates into the analysis passage of the test cell. Ambient air is employed to convey the particulates through the analysis cell, no special conveying gasses nor dispersant liquids are required.

Further, because of the small overall size of the analysis cell, it may be employed within the test well of a conventional particle analyzer previously used for liquid-borne samples. The vibratory sifter cup and vibration drive therefor can easily be stacked above this test well of the conventional particle analyzer so that no additional bench-top space is required. Because the outlet port of the analysis cell is disposed at the top of the ascending leg of the J-shaped cell flow path, connection of the cell to an external vacuum source is simplified. In fact, the vacuum source plumbing can exit out the top of the test well opening of the conventional particle analyzer with no need for extensive changes to the latter.

Still further, the vibratory motion imposed on the sample cup is chosen to be an orbital oscillation in a vertical plane. This vertical oscillation motion of the sample cup is thought to provide a monotonically increasing rate of particle feed from the bulk sample as a function of oscillation rate. Also, the orbital oscillatory vibration is not prone to generate either audible noise nor structural noise, which could possibly impair the delicate optical system used in diffraction analysis.

The above, and additional advantages of the present invention will be appreciated from a reading of the following detailed description of a single preferred embodiment of the invention, taken in conjunction with the appended drawing figures, in which:

BRIEF DESCRIPTION OF THE DRAWING FIGURES

FIG. 1 provides a perspective view of a particle analyzer embodying the invention;

DETAILED DESCRIPTION OF A PREFERRED EMBODIMENT OF THE INVENTION

Figure 1:
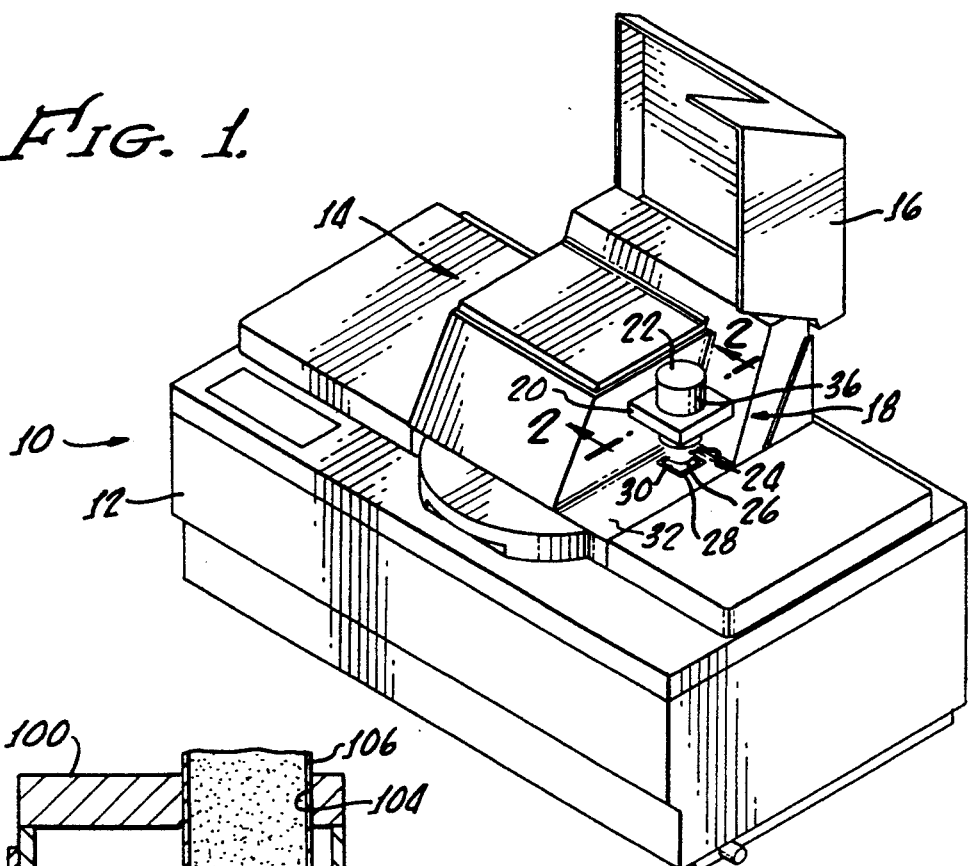

Viewing FIG. 1, a particle analyzer 10 includes a housing 12 which may sit upon a bench top (not shown). The particle analyzer 10 includes a dry particle feeder 14 which is stacked upon the remainder of the analyzer 10, and having a cover portion 16, shown in an open position. The open cover 16 reveals a sample chamber 18 of the dry particle feeder 14 wherein is disposed a vibratory sieve cup clamp 20 holding a sample sieve cup 22. Sample sieve cup 22 includes a funnel-like lower portion 24 extending downwardly into the open upper end or mouth 26 of a conduit member 28. The conduit member 28 extends upwardly through an opening 30 defined by a cover plate portion 32 of the dry particle feeder 14. Cover plate 32 spans across an analysis cell well (not seen in FIG. 1, but referenced with numeral 34 in FIG. 2). The sample sieve cup includes an open cylindrical portion 36 into which a powdered, or granular, or otherwise particulate sample may be placed for particle size analysis using the analyzer 10.

Figure 4:
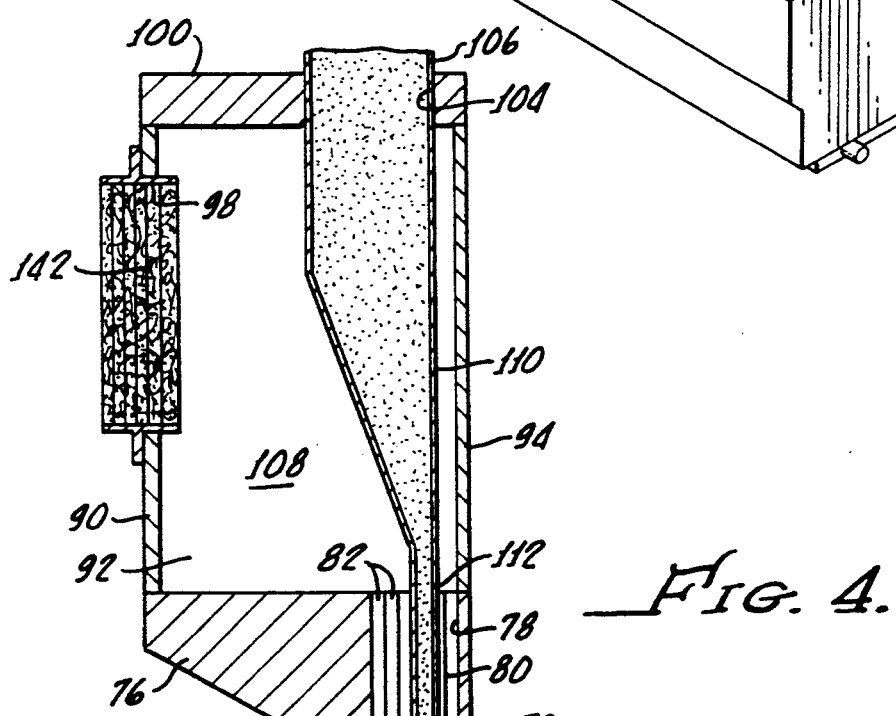
FIG. 4 provides a left-side elevation view partly in cross section taken at lines 4—4 of FIGS. 1 and 2, of the portion of the particle analyzer seen in FIG. 2.
Figure 2:
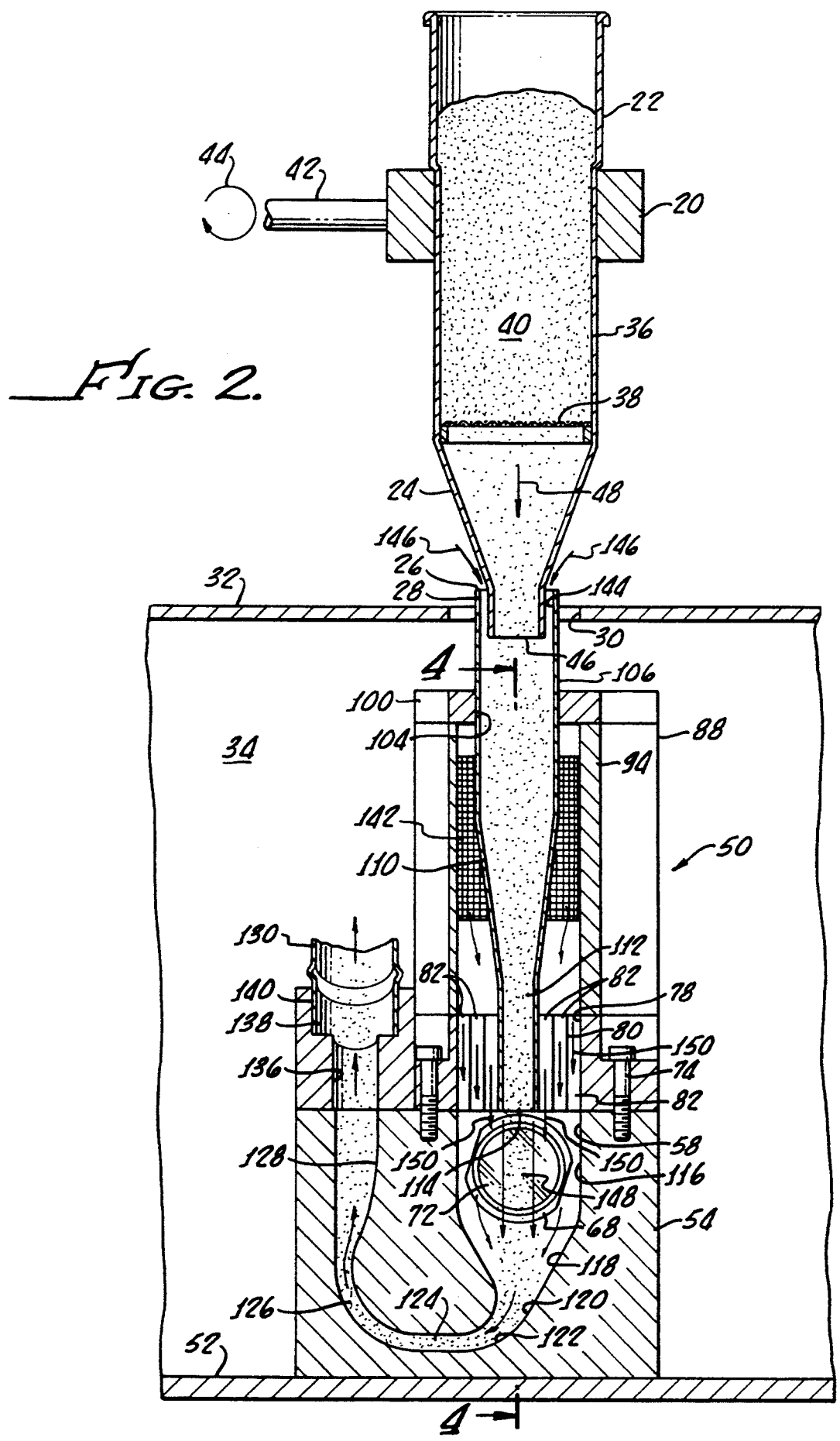
FIG. 2 is a fragmentary elevation view, partially in cross section taken at line 2—2, of a portion of the particle analyzer seen in FIG. 1.
Figure 3:
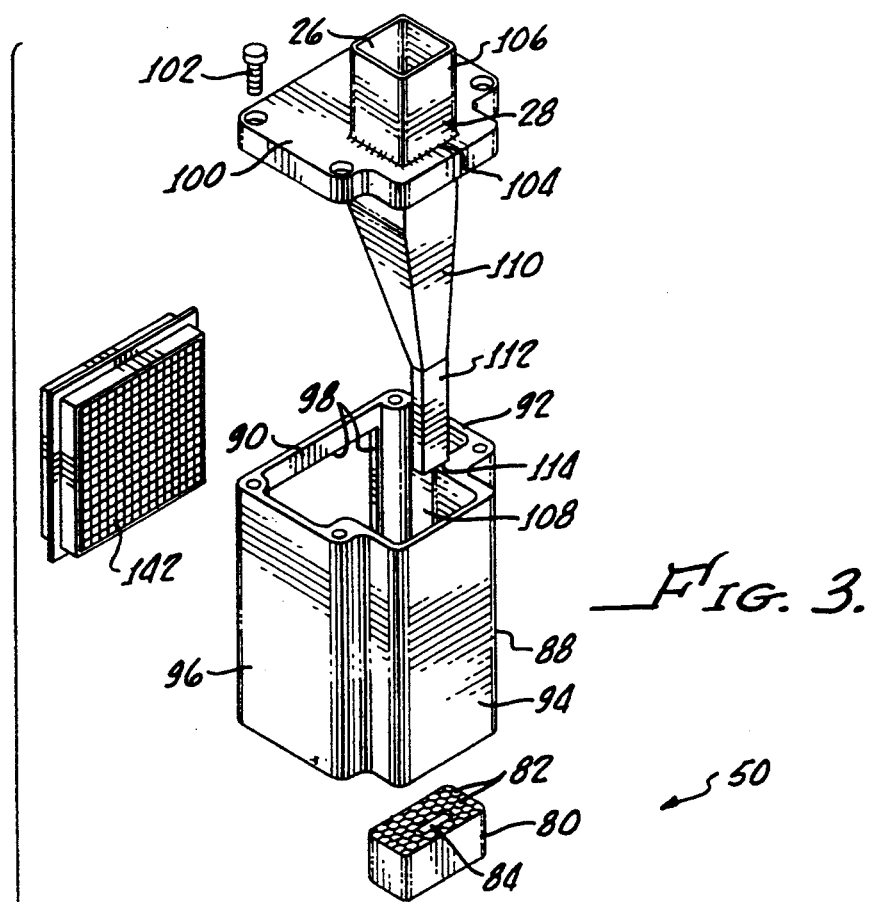
FIG. 3 is an exploded perspective view of a portion of the particle analyzer seen in FIG. 2.
Figure 3:
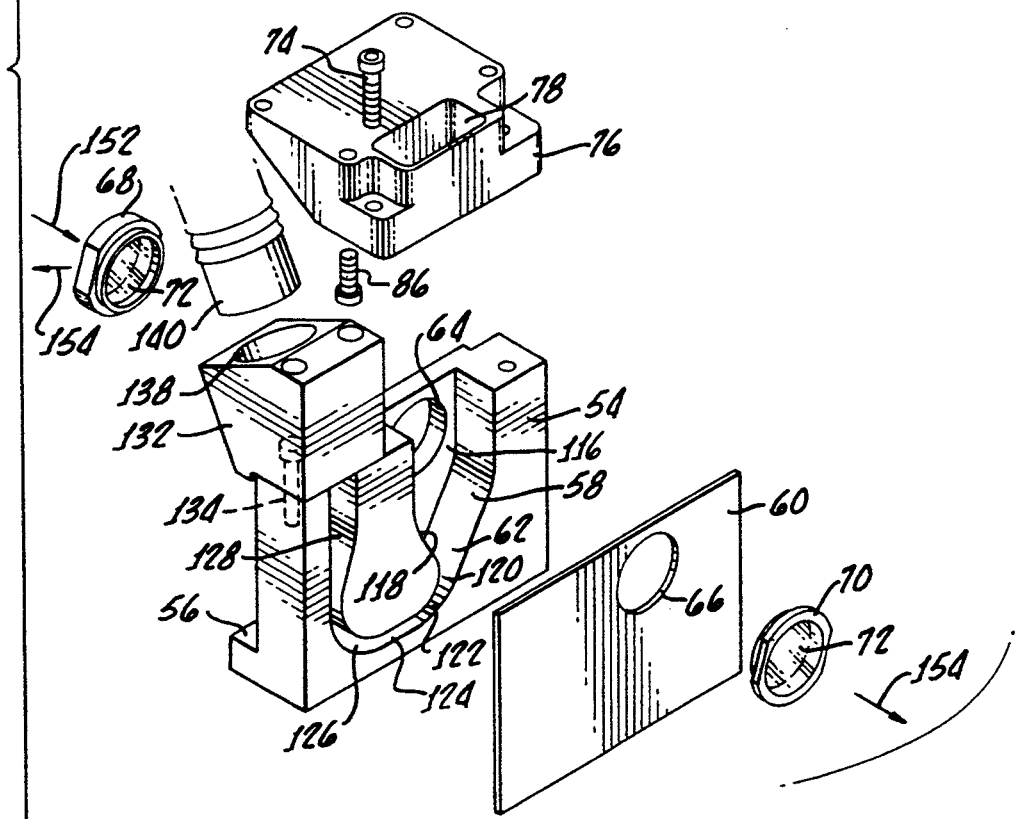

Viewing now FIGS. 2-4 in conjunction, with particular attention to FIG. 2, the sample sieve cup 22 is seen to include a sieve screen 38, above which is disposed a bulk sample of particulate material 40, the particle size distribution of which is to be determined with analyzer 10. Sample sieve cup 22 is subjected to a vibratory motion imposed upon the cup clamp 20 through a supporting arm 42 extending laterally into the chamber 18 from the left-hand part of the dry particle feeder 14, as seen in FIG. 1. Preferably, the vibratory motion imposed upon the sample sieve cup 22 is an orbital motion, and is oriented in a vertical plane, as depicted by arrow 44. As was pointed out above, the vertical orbital oscillation of the sample cup 22 is believed to be advantageous in terms of the avoidance of both audible and structural noise in the environment of the analyzer 10. Such noise could possibly interfere with or impair the delicate optical system used in diffraction analysis.

The vibratory motion imposed upon the sample cup 22 causes particles from the bulk 40 to drizzle through the screen 38, and to be discharged from the open lower end 46 of the funnel portion 24 of the sample cup, as is indicated by arrow 48. The applicant believes that the vertical orbital oscillation of the sample cup 22 results in the particles being drizzled therefrom at a monotonic rate as a function of oscillation rate. Consequently, control of the drizzle rate of the particles 48 from the sample cup is easier to achieve, is more predictable, and improved accuracy and repeatability of test results are obtained. Within the analysis cell well 32 of the particle analyzer 10, is disposed an analysis cell assembly, generally referenced by the numeral 50, and including the conduit member 28 which extends upwardly through the opening 30 of cover plate 32.

Analysis cell assembly 50 sits upon a floor 52 of the well 34, and a base portion 54 of the analysis cell includes a projecting flange portion 56 (best seen in FIG. 3), by which the cell assembly may be clamped into position in a cell socket (not shown) on floor 52. Base portion 54 defines a generally U-shaped recess 58, and sealingly carries a closure plate 60 cooperating with the base portion 54 to bound a flow path portion 62, which is described in greater detail below. Importantly, in order to provide windows to the analysis cell, the base portion 54 and closure plate 60 each define a respective one of a pair of aligned opposite apertures 64,66. Respectively received sealingly in the apertures 64,66 are one of a pair of window carrier rings 68,70. The rings 68,70 each sealingly include a transparent glazing material 72.

Carried upon the base portion 54 and secured sealingly thereto by a pair of fasteners 74 (only representative ones of the fasteners are shown in FIG. 3), is a plenum floor member 76. The plenum floor member defines a downwardly extending through outlet opening 78, which is rectangular in plan view. Carried in and filling the opening 78 is a block 80 of honeycomb material defining plural comparatively small vertically-extending through hexagonal passages 82, and one larger through rectangular passage 84. Also carried upon and sealingly secured to the plenum floor member 76 by fasteners 86, is a plenum wall member 88. The wall member 88 includes four upstanding walls 90–96, one of which (90) defines a rectangular inlet window 98. Atop the plenum wall member and carrying the conduit member 28, is sealingly secured a plenum top member 100 sealingly secured by fasteners 102. The top member defines an opening 104 in which is sealingly secured, as by welding, the upper cylindrical portion 106 of the conduit member 28. It is the upper extent of this upper portion 106 of conduit member 28 external to the top member 100 which is seen in FIG. 1 extending upwardly through the opening 30 of cover plate 32 and defining mouth 26. Plenum floor member 76, wall member 88, and top member 100 cooperate to define a plenum chamber 108 which is closed except for inlet 98 and outlet opening 78. Within the chamber 108, the conduit member 28 includes a convergent portion 110 leading from the upper portion 106 smoothly to a cylindrical lower elongate portion 112. Lower portion 112 of the conduit member 28 extends through the passage 84 of the block 80 to terminate in an open end 114 at about the same level as the lower side of the block 80, which defines the lower extent of the passages 82.

Considering now the recess 58 of base member 54 in greater detail, it is seen that this recess is U-shaped in plan view so that the flow path portion 62 is rectangular in plan view. A first cylindrical analysis-passage part 116 of the flow path portion 62 is congruent with the passage 84, and includes the windows (64–72). Almost immediately below the windows (64–72), the flow path portion 62 includes a convergent part, referenced with the numeral 118. This convergent flow passage part leads smoothly to a throat part 120 which immediately (at 122) turns about 90 degrees to extend horizontally (as is referenced with numeral 124) a short distance adjacent the lower extent of the base portion 54. After this short horizontal run 124, the throat part 120 again turns about 90 degrees (at 126) to extend upward a short distance. The throat part 120 then leads smoothly to a divergent flow path part 128.

In order to provide connection between the flow path portion 62, and a source of vacuum at a hose 130, the analysis cell includes an exit fitting member 132. Exit fitting 132 is sealingly secured to the base portion 54 by fasteners 134. The exit fitting 132 defines a passage 136 congruent with the flow path portion divergent part 128 (viewing FIG. 2), and defines a tapered bore 138 for frictionally receiving the tapered end portion 140 of the vacuum hose in flow communication with the passage 136. Vacuum hose 130 leads to a conventional industrial vacuum cleaner (not shown) with a fine filter element for insuring that the particles under test are not blown out into the ambient. In order to further insure that the test results are not influenced undesirably by dust in the ambient, the window 98 of wall member 88 also receives a friction-fit fine filter pack 142.

Having considered the structure of the analysis cell assembly 50, attention may now be directed to the use of the particle analyzer 10. As was described above, the sample cup 22 drizzles particles from the bulk sample 40 into the upper end or mouth 26 of the conduit member 28, recalling arrow 48. Because the funnel portion 24 of the sample cup 22 is smaller than the mouth 26 of the conduit member 26, there is defined cooperatively therebetween a first sheath air inlet 144 receiving ambient air (as represented by arrows 146) for flow as a sheath or boundary layer between the particle drizzle 48, and the walls of the conduit member 28, remembering that ambient air flow is caused by vacuum from the vacuum source hose 130. The particle drizzle and first sheath air travel together downwardly in the conduit portions 106 and 110, with the latter convergent conduit portion effecting an increase of the flow velocity. Gravitational influence on the drizzled particles is thought to possibly assist this particle acceleration, and the design of the analysis cell assembly 50 is such that opposition to gravitational force is not required at any point. The first sheath air flow keeps the particles from contacting or adhering to the walls of the conduit member 28, the inner surfaces of which are readily accessible and easy to clean should wall contamination occur. Subsequently, the elongate cylindrical conduit portion 112 columnates the air flow and drizzled particles so that the latter are discharged as a particle curtain 148 into the analysis passage 116 from outlet 114. Also delivered into the analysis passage 116 is a descending column of second sheath air 150 from the passages 82 and plenum chamber 108. This air is admitted to the chamber 108 via the window 98 and filter pack 142 therein. Importantly, the total ambient air flow resistances to the outlet 114 of conduit member 28, and to the outlets of the passages 82 is matched equally to one another so that these air flows have substantially equal velocities. Thus, the air flow from passages 82 unites with and surrounds the air flow 148 with curtained drizzling particles 48.

In the analysis passage 116 of the analysis cell assembly 50, beamed light or other electromagnetic radiation (represented by arrow 152, and all referred to collectively herein as, "optical interrogation beams") is directed through one of the windows (64–72). Forward and back scattered light, as well as obscuration and diffraction information from the curtained particulates 148 is represented by arrows 154, and is incident on receptors 156 for further analysis in conventional ways. Subsequent to the analysis passage 116, the particles are drawn through the remainder of the flow path portion 62, and out vacuum hose 130. Because the particles are deeply sheathed in the first and second sheathing air flows, they do not generally impact on, adhere to, or settle out on the walls of the analysis cell assembly. However, should some particles ever remain in the analysis cell assembly 50, any wall contamination will occur below the analysis passage 116 and, therefore, will not affect subsequent measurements. Moreover, this assembly is easily disassembled and cleaned, and its resulting cleanliness can be visually verified.

Consideration of the above description of the disclosed preferred embodiment will reveal that the particles are drizzled straight downwardly from their bulk sample into the analysis passage. The design of the analysis cell does not fight or try to avoid the effect of gravitational influence on the particles, but instead uses this force to advantage. It follows that particle dropout is simply not a problem from which the Applicants' invention could suffer. Also, the conduit member 28 and base portion 54 with U-shaped flow path portion 62 cooperatively define a particle flow path which is generally of J-shape. That is, the conduit member 28 forms the upper reach of the J-shape, while the U-shaped flow path portion 62 completes the lower hook of the J-shape. The resulting analysis cell assembly is small and can be inserted into the analysis well of a conventional particle analyzer previously used for testing liquid-borne particulates. The curtained drizzling particles are not perturbed or baffled or turned from their downward course until after they have passed the windows of the analysis passage and have been interrogated. Thus, the accuracy of the presently disclosed dry particle analysis cell is thought to be without equal heretofore.

While the present invention has been depicted, described, and defined by reference to a particular preferred embodiment of the invention, such reference does not imply a limitation on the invention, and no such limitation is to be inferred. Only the spirit and full scope of the appended claims is intended as a limitation on the invention. Further, the invention is subject to modifications and variations which will suggest them selves to those skilled in the pertinent art. Such modifications and variations are intended to fall within the scope of the appended claims.

We claim:

1. A dry particle analyzer comprising: means for drizzling particles from a bulk sample thereof, means for providing a downward flow of first sheath ambient air around said drizzling particles, means for downwardly columnating the first sheath air flow and drizzling particles, means for providing a downward and columnar flow of second sheath ambient air around said columnated first sheath air and drizzled particles and substantially in velocity union therewith, and means defining a vertically downwardly extending optical analysis cell passage receiving the unified downward flow of drizzled particles and first and second sheath air for columnated downward flow therein, whereby the drizzled particles flow downwardly continuously from said bulk sample and through said analysis cell passage means.

2. The dry particle analyzer of claim 1 further including
exit passage means for receiving from said analysis cell passage means said downward flow of drizzled particles and sheath air flows and turning the combined flow through substantially 180 degrees for upward exit flow, whereby said analysis cell and exit passage means cooperatively define generally a J-shape.

3. The dry particle analyzer of claim 2 wherein said exit passage means defines a convergent-divergent venturi nozzle shape.

4. The dry particle analyzer of claim 3 wherein said exit passage means further includes a divergent pressure-recovery section leading to an exit port.

5. The dry particle analyzer of claim 4 including a housing member defining therein said analysis cell passage means and said exit passage means, said housing sealingly carrying opposed transparent windows bounding said analysis cell passage, and providing for optical interrogation of said drizzled particles.

6. The dry particle analyzer of claim 1 wherein said means for drizzling particles from a bulk sample thereof includes a sieve cup, and means for vibrating said sieve cup.

7. The dry particle analyzer of claim 6 wherein said means for vibrating said sieve cup includes means for imposing a vertical oscillation on said sieve cup.

8. The dry particle analyzer of claim 7 wherein said means for imposing said vertical oscillation on said sieve cup includes means for imposing a vertical orbital oscillation to said sieve cup.

9. The dry particle analyzer of claim 1 wherein said means for providing said first sheath air flow around said drizzling particles includes a conduit extending vertically downwardly from an upwardly open mouth and receiving therein a lower exit portion of said sieve cup, said lower exit portion of said sieve cup and said conduit mouth cooperating to define a first ambient air inlet circumscribing said sieve cup exit portion.

10. The dry particle analyzer of claim 9 wherein said means for downwardly columnating said first sheath air flow and drizzled particles includes said conduit including a convergent flow velocity-increasing section below said mouth thereof, and said convergent section blending smoothly into a cylindrical conduit section extending through said means for providing said second sheath air flow.

11. The dry particle analyzer of claim 10 wherein said means for providing said second sheath air flow includes a plenum chamber means around said conduit, said plenum chamber means defining an ambient air inlet and having a downwardly open air outlet through which extends said cylindrical conduit section, said plenum chamber means including at said air outlet thereof a cellular air flow guide surrounding said cylindrical conduit section.

12. The dry particle analyzer of claim 11 wherein said plenum chamber means further includes an air filter at said ambient air inlet.

13. The dry particle analyzer of claim 1 including means for delivering said drizzled particles as a curtain of downwardly flowing particles.

14. The dry particle analyzer of claim 13 including said means for providing said first sheath air including an elongate rectangular outlet out of which said drizzled particles and first sheath air flow.

15. A dry particle analyzer apparatus comprising drizzling means for dispersing particulates from a bulk sample thereof downwardly at a selected metered rate, a conduit defining an upwardly open mouth receiving the drizzling particles and a first vertically downward flow of ambient sheath air, said conduit directing said particulates and first sheath air still further downwardly along a convergent conduit section, thereby effecting an increase of flow velocity through an externally surrounding plenum of second sheath air, said surrounding plenum providing an inlet through which enters ambient air and said plenum channels air therein downwardly therefrom through a plenum exit including a multi-cellular flow-columnator around the conduit, said conduit includes an elongate cylindrical flow-columnating exit portion extending through the flow-columnator, and each of said conduit and said plenum with flow columnator has generally the same total air flow resistance to produce substantially the same air flow velocity for both the first and second sheath air flows to provide a homogeneous descending column of air which includes a centralized flow stream of air with the drizzle of particles at a known location in the air flow column, and disposed below the convergent conduit and second sheath air plenum and in sealed relation with the latter is a planar analysis cell defining an air flow path generally of J-shape, the analysis cell defines a vertically downwardly extending analysis passage having opposite transparent windows for passage of test radiation beams perpendicular to the plane of the J-shape, and below the analysis passage the analysis cell includes side walls defining a sub-critical convergent-divergent venturi nozzle shape which turns the air and particulate flow 180 degrees at the bottom of the J-shape and leads upwardly as a divergent pressure-recovery diffuser to an exit port.

16. The dry particle analyzer of claim 15 wherein said means for drizzling particles from a bulk sample thereof includes a sieve cup, and means for vibrating said sieve cup.

17. The dry particle analyzer of claim 16 wherein said means for vibrating said sieve cup includes means for imposing a vertical oscillation on said sieve cup.

18. The dry particle analyzer of claim 17 wherein said means for imposing said vertical oscillation on said sieve cup includes means for imposing a vertical orbital oscillation to said sieve cup.

19. The dry particle analyzer of claim 15 wherein said secondary sheath air plenum further includes an air filter at said inlet.

20. A method of dry particle analysis, said method including the steps of: drizzling particles from a bulk sample thereof, providing a downward flow of first sheath ambient air around said drizzling particles, downwardly columnating the first sheath air flow and drizzling particles, providing a downward and columnar flow of second sheath ambient air around said columnated first sheath air and drizzled particles and substantially in velocity union therewith, uniting said first and said second air flows, defining a vertically downwardly extending optical analysis cell passage below and downwardly receiving the unified downward flow of drizzled particles and first and second sheath air flows for continued downward flow therein, and optically interrogating said drizzled particles in said analysis cell passage, whereby the drizzled particles flow continuously downwardly from said bulk sample and through said analysis cell passage.

21. The method of claim 20 further including the steps of flowing said unified flow of drizzled particles and first and second sheath air flows through a convergent-divergent venturi nozzle, and turning said unified flow substantially 180 degrees while traversing said venturi nozzle, to flow upwardly to an outlet port.

* * * * *